(12) United States Patent
Levi et al.

(10) Patent No.: US 10,500,124 B2
(45) Date of Patent: Dec. 10, 2019

(54) METHODS, DEVICES AND SYSTEMS FOR ORTHOPTICS (71) Applicants: University of Rochester, Rochester, NY (US); The Regents of the University of California, Oakland, CA (US)

(72) Inventors: Dennis Levi, Berkeley, CA (US); Daphne Bavelier, Le Grand-Saconnex (CH); Martin S. Banks, Berkeley, CA (US)

(73) Assignees: University of Rochester, Rochester, NY (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 15/748,578

(22) PCT Filed: Aug. 31, 2016

(86) PCT No.: PCT/US2016/049731
§ 371 (c)(1),
(2) Date: Jan. 29, 2018

(87) PCT Pub. No.: WO2017/040687
PCT Pub. Date: Mar. 9, 2017

(65) Prior Publication Data
US 2018/0214339 A1 Aug. 2, 2018

Related U.S. Application Data
(60) Provisional application No. 62/214,112, filed on Sep. 3, 2015.

(51) Int. Cl.
A61H 5/00 (2006.01)
A61B 3/08 (2006.01)
A63F 13/52 (2014.01)
A63F 13/837 (2014.01)

(52) U.S. Cl.
CPC ............... *A61H 5/005* (2013.01); *A61B 3/08* (2013.01); *A63F 13/52* (2014.09); *A63F 13/837* (2014.09); *A61H 2201/5007* (2013.01); *A61H 2201/5012* (2013.01); *A61H 2201/5043* (2013.01); *A61H 2201/5046* (2013.01); *A61H 2201/5048* (2013.01); *A61H 2201/5097* (2013.01)

(58) Field of Classification Search
CPC ............ A61H 5/005; A61H 2201/5097; A61H 2201/5012; A61H 2201/5007; A61H 2201/5048; A61H 2201/5046; A61H 2201/5043; A63F 13/837; A63F 13/52; A61B 3/08; G07F 17/3267; G05G 9/047
USPC .................................................. 351/200, 201
See application file for complete search history.

(56) References Cited

U.S. PATENT DOCUMENTS

2012/0127426 A1   5/2012  Backus et al.
2014/0211167 A1   7/2014  Lewis
2018/0116510 A1*  5/2018  Freeman .................. A61B 3/06
2018/0200142 A1*  7/2018  Freeman ................ G16H 40/20

* cited by examiner

*Primary Examiner* — Tuyen Tra
(74) *Attorney, Agent, or Firm* — Rudy J. Ng; Bozicevic, Field & Francis LLP (57) ABSTRACT

Provided herein is an orthoptic method of improving depth-perception in an individual. Devices, systems and kits for performing the present method are also provided.

37 Claims, 4 Drawing Sheets

METHODS, DEVICES AND SYSTEMS FOR ORTHOPTICS

CROSS-REFERENCE TO RELATED APPLICATIONS

This application claims the benefit pursuant to 35 U.S.C. § 119(e) of U.S. Provisional Application No. 62/214,112, filed Sep. 3, 2015, the disclosure of which is incorporated herein by reference in its entirety.

REFERENCE TO GOVERNMENT SUPPORT

This invention was made with government support under Grant Number RO1EY020976 awarded by the National Eye Institute. The government has certain rights in the invention.

BACKGROUND

The ability to see in three dimensions is among the most critical of visual functions. For example, vision is used to guide body movements, which would essentially be impossible without accurate depth perception. However, more than 5% of the US population suffers from stereo-deficiency or abnormal depth perception.

Products to alleviate stereo deficiency on the market include a set of eye-training exercises primarily designed for children. These exercises are collectively called orthoptics. Recent work has emphasized dichoptic training, in which the stimuli to the two eyes have different strengths—i.e., higher contrast in the weak eye and lower contrast in the strong eye. This approach can equalize the input from the two eyes to the brain, and may reduce suppression. Suppression of an eye is a subconscious adaptation by a person's brain to eliminate the symptoms of disorders of binocular vision such as strabismus, convergence insufficiency and aniseikonia. For example, the brain can eliminate double vision by ignoring all or part of the image of one of the eyes. However, merely reducing suppression may not correlate to improved visual function.

SUMMARY

Provided herein is an orthoptic method, as well as devices and systems for implementing an orthoptic method. An implementation of the method includes the steps of i) displaying one or more stereoscopic objects on a user interface configured to present one or more depth-perception tasks to an individual during a first time period, where each of the one or more depth-perception tasks has a difficulty level for the individual to perform each of the one or more depth-perception tasks, and each stereoscopic object is associated with one or more monocular depth cues and one or more binocular depth cues, and where a strength of the monocular depth cues is correlated with the difficulty level; and ii) titrating the strength of the monocular depth cues during the first time period, in a manner sufficient to reduce a dependence of the individual on the monocular depth cue for preforming the one or more depth-perception tasks.

In some embodiments, the monocular depth cues include one or more of motion parallax, relative size, familiar size, cast shadows, occlusion, accommodation, texture gradient, linear perspective, aerial perspective, shading, lighting, and defocus blur.

In some embodiments, the binocular depth cues include binocular disparity and/or vergence.

In some embodiments, the titrating step ii) includes weakening or strengthening the monocular depth cues based on a performance of the individual for the one or more depth-perception tasks.

In some embodiments, the titrating step ii) includes weakening or strengthening the monocular depth cues in a step-wise manner.

In some embodiments, the method includes receiving an input from the individual through an input device, where the input indicates whether the individual has progressed toward a goal.

In some embodiments, the method includes providing the individual a feedback that notifies the individual whether there has been progress toward the goal.

In some embodiments, the goal includes a plurality of depth-perception tasks to be performed by the individual.

In some embodiments, the input indicates the difficulty level experienced by the individual, and the titrating step ii) includes weakening an initial monocular depth cue prior to a time point during the first time period to a second monocular depth cue strength after the time point, where the time point is chosen arbitrarily or is chosen based on the difficulty level experienced prior to the time point.

In some embodiments, the time point is chosen so as to maintain a threshold level of difficulty before and after the time point.

In some embodiments, the depth-perception task is part of a scrolling shooter game.

In some embodiments, the scrolling shooter game includes a task for the individual to align a first stereoscopic object and a second stereoscopic object in a perceived three-dimensional space in the user interface by having the individual control a three-dimensional position of the first stereoscopic object in the perceived three-dimensional space.

In some embodiments, the method further includes assessing stereoacuity and/or motion-in-depth acuity of the individual.

In some embodiments, the assessing stereoacuity and/or motion-in-depth acuity includes presenting one or more n-alternative forced choice tasks, or one or more odd-man-out tasks to the individual through the user interface.

In some embodiments, the odd-man-out task includes a task for the individual to select, in the user interface: a first stereoscopic object among a plurality of stereoscopic objects based on the perceived difference in depth of the first stereoscopic object relative to the perceived depths of the other stereoscopic objects; and/or a second stereoscopic object among a plurality of stereoscopic objects based on a perceived change in depth of the second stereoscopic object relative to the perceived change in depths of the other stereoscopic objects.

In some embodiments, the n-alternative forced choice task or odd-man-out task defines a difficulty level for the individual to perform the n-alternative forced choice task or odd-man-out task, and the n-alternative forced choice task or odd-man-out task difficulty level is individually titrated.

In some embodiments, the displaying includes displaying a first subset of the one or more stereoscopic objects on the user interface such that the stereoscopic objects in the first subset are perceived at a periphery of the individual's visual field.

In some embodiments, the displaying includes displaying a second subset of the one or more stereoscopic objects on the user interface such that the stereoscopic objects in the second subset is perceived by the individual to be changing depths.

In some embodiments, a third subset of the one or more stereoscopic objects includes one or more state-dependent stereoscopic objects that are each in one of two or more states defining a first and second states, where a state-dependent stereoscopic object in a first state is associated with a first state sensory cue that is different from a second state sensory cue associated with the state-dependent stereoscopic object in a second state, where a state-dependent stereoscopic object alternates among the two or more states at a time interval within the first time period.

In some embodiments, the displaying includes displaying a stereoscopic object in the third subset on the user interface for the stereoscopic object to be perceived by the individual as being at a different depth from depths of stereoscopic objects that are not in the third subset.

In some embodiments, the depth-perception task has a threshold level of accuracy for the individual to determine a three-dimensional position of the stereoscopic objects, where the threshold level of accuracy is correlated with the difficulty level, and the method further includes changing the threshold level of accuracy over the first time period such that the reduction in the strength of the one or more monocular depth cues is compensated for by the change in the threshold level of accuracy.

In some embodiments, the method further includes, before the displaying step i): 1) providing the individual, through the user interface, with a training goal for the individual to achieve during a second time period, where the training goal defines a difficulty level for achieving the training goal by the individual; 2) displaying on the user interface: a first image to a visual field of a first eye of the individual; and a second image to a visual field of a second eye different from the first eye of the individual, where the first and second images include one or more dichoptically-presented vergence cues and the training goal includes fusing the first and second images, where the dichoptically-presented vergence cues define a dichoptically-presented vergence cue strength correlated with the difficulty level; 3) receiving an input from the individual through the input device, the input indicating whether the individual has achieved the training goal; and 4) providing the individual a feedback that indicates to the individual whether the individual has achieved the training goal.

In some embodiments, the dichoptically-presented cues are corrected to account for the individual's vergence deviation.

In some embodiments, the individual's vergence deviation is determined by: displaying, on the user interface, a stereoscopic image including a stereoscopic object and dichoptic nonius lines; adjusting the horizontal displacement of the dichoptic nonius lines such that the dichoptic nonius lines are perceived by the individual to be collinear, thereby obtaining a full correction value for the individual's vergence deviation; displaying on the user interface, the stereoscopic image with a correction for the individual's vergence deviation based on the full correction value; reducing the correction such that the stereoscopic image is perceived to appear in double, thereby obtaining a lesser correction value for the individual's vergence deviation; and setting the individual's vergence deviation to be the midpoint between the full and lesser correction values.

In some embodiments, the method further includes before the displaying step i): displaying on the user interface: a first image to a visual field of a first eye of the individual; and a second image to a visual field of a second eye different from the first eye of the individual, wherein the first and second images have the same absolute contrast level; and reducing the contrast in the image perceived to have the higher contrast by the individual to reduce the difference in contrast in the images perceived by the first eye and the second eye.

In some embodiments, the feedback is a visual, tactile and/or auditory feedback.

In some embodiments, the method includes positioning a visual display including the user interface over a visual field of the individual, where the visual display is configured to display the stereoscopic image comprising the stereoscopic object on the user interface.

In some embodiments, the individual is diagnosed as having abnormal depth perception.

In some embodiments, the individual is diagnosed with amblyopia and/or strabismus.

In some embodiments, the individual has a normal depth perception.

Aspects of the present disclosure include a device for preforming the method described herein. In some embodiments, the device includes: a visual display including a user interface configured to display one or more stereoscopic objects to the individual, each stereoscopic object associated with one or more monocular depth cues and one or more binocular depth cues; a processor; and a non-transient computer-readable medium including instructions that, when executed by the processor causes the visual display to: display the one or more stereoscopic objects on the user interface; and titrate the strength of the one or more monocular depth cues.

In some embodiments, the device is configured to receive an input from the individual through an input device.

Aspects of the present disclosure include an orthoptic system that includes: a processor; a user interface configured to display one or more stereoscopic objects to an individual, each stereoscopic object associated with one or more monocular depth cues and one or more binocular depth cue; and a non-transient computer-readable medium including instructions that, when executed by the processor causes the user interface to: display the one or more objects on the user interface; and titrate the strength of the monocular depth cues.

In some embodiments, the system is configured to interface with an input device configured to receive an input from the individual.

In some embodiments, the system is configured to interface with a feedback delivery device configured to provide a feedback to the individual based on the received input.

In some embodiments, the instructions, when executed by the processor, cause the user interface to perform the method as described herein.

BRIEF DESCRIPTION OF THE FIGURES

The drawings, described below, are for illustration purposes only of certain embodiments of the present disclosure. The drawings are not intended to limit the scope of the present disclosure in any way.

DEFINITIONS

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some examples of embodiments of methods and materials are now described.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

A "subset" may contain one or more members within a larger group of members.

"Individual" and "user" are used interchangeably to refer to an animal with at least two eyes that are used to perceive an object. The individual may be a bird, or a mammal, e.g., a cat, dog, monkey, non-human primate, or a human.

"Task," as used herein, refers to an action, or series of actions, for an individual to take within an environment defined by a set of rules. An individual "performs" a task when the individual takes the action or series of actions defined by the rules. A collection of tasks may define a "goal" that the individual can "progress toward" by performing one or more tasks in the collection of tasks.

"Perception" as used herein, refers to a recognition, either conscious or not, by an individual of a sensory experience. In some cases, perception may be equivalent to "sensation," e.g., when the subjective experience of the individual is not readily apparent, e.g., in a non-human individual.

"Depth" refers to the distance between an individual and a visual target in three-dimensional space perceived or sensed by the individual. A "depth-perception task" is a task that requires the user to perceive or sense the depth of an object to perform the task successfully. A "depth cue" is a visual characteristic associated with an object that contributes to perception of the object's depth characteristics (three-dimensional shape, three-dimensional orientation, three-dimensional movement, etc.) by an individual when provided with the depth cue. A "monocular depth cue" is a depth cue that can contribute to perception of the object's depth characteristics by an individual without the depth cue being viewed by both eyes of the individual (i.e., when viewed by one eye of the individual). A "binocular depth cue" is a depth cue that must be viewed by both eyes of an individual to provide a perception of the object's depth characteristics by the individual. A depth cue may be characterized by a "cue strength" or "strength", which represents a measure of how much the depth cue contributes to the perception or sensing of depth by the individual.

"Titrate", as used herein, refers to an action or process, or a series of actions or processes, which causes a quantitative change in a variable of interest, usually in order to bring the variable within a target range or otherwise cause an intended outcome. In some contexts, titrating a strength of a visual depth cue, e.g., a monocular depth cue, provided to an individual may include adjusting (weakening or strengthening) the sensory cue based on how accurately the individual is visually perceiving depth at the current strength of the sensory depth cue, thereby changing the accuracy with which the individual is visually perceiving depth to a desired level or within a desired range. In some cases, titrating may include changing the strength of the sensory cue regardless of the individual's ability to perceive depth so as to introduce an element of randomness.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that embodiments of the present disclosure are not limited in its application to the details of construction, the arrangements of components, category selections, weightings, pre-determined signal limits, or the steps set forth in the description or drawings herein. The present disclosure may encompass other embodiments and may be practiced or be carried out in many different ways.

DETAILED DESCRIPTION

Methods

Figure 1:
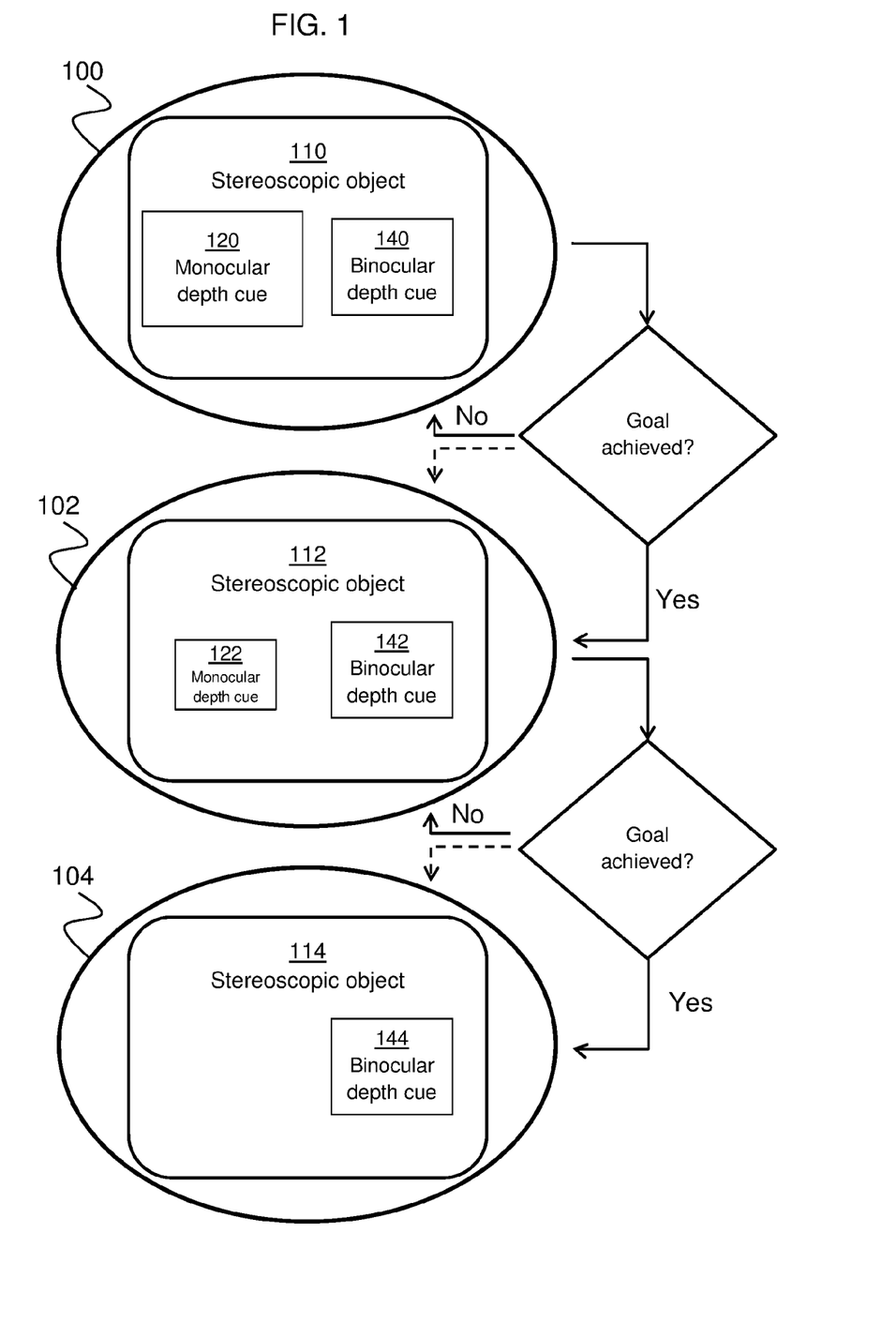
FIG. 1 shows a schematic diagram and flow chart of an orthoptic method, according to embodiments of the present disclosure.

With reference to FIG. 1, an orthoptic method of the present disclosure includes providing an individual, e.g., a user, with one or more depth-perception tasks 100 using a user interface that is configured to display a stereoscopic object 110. The stereoscopic object is initially associated with one or more monocular depth cues 120 and one or more binocular depth cues 140, the combination of which helps the user perceive the three-dimensional properties of the object, such as the position of the object in depth relative to the user, the depth of the object relative to other objects visible in the user interface, the motion of the object in three-dimensions, etc. The depth perception task requires the user to properly perceive the depth of stereoscopic objects in the user interface and take action according to the perceived depth of the stereoscopic objects. Depending on the individual, the individual may rely solely on the monocular depth cues or the binocular depth cues, rely relatively more on one over the other, or rely equally on both. The reliance of an individual on the monocular depth cues can be reduced, according to embodiments of the present method, such that the individual relies more on the binocular depth cues to perceive depth and three-dimensional space.

Thus, in certain embodiments, the method includes the step of displaying one or more stereoscopic objects to an individual during a first time period. The one or more stereoscopic objects may be displayed on a user interface. For instance, the user interface may be configured to present one or more depth-perception tasks for an individual to perform during the first time period. Each stereoscopic object displayed to the individual is associated with one or more monocular depth cues and one or more binocular depth cues. As described herein, the one or more monocular depth cues and one or more binocular depth cues are observed by the user who uses the one or more monocular depth cues and one or more binocular depth cues to perceive the three-dimensional properties of the stereoscopic object being displayed to the individual. Based on the individual's visual perception of the stereoscopic object, the user may perform one or more depth-perception tasks. For example, the depth-perception task may include aligning the relative positions of two or more objects on the user interface. In some cases, the individual may align two or more objects in a horizontal dimension on the user interface. In some cases, the individual may align two or more objects in a vertical dimension on the user interface. In some cases, the individual may align two or more objects in a depth dimension on the user interface. In some cases, the individual may align two or more objects in a combination of two or more of a horizontal dimension, a vertical dimension, and/or a depth dimension on the user interface (i.e., alignment in a two or three-dimensional space).

The monocular depth cues may include any suitable monocular depth cues, and may include, without limitation, motion parallax, relative size, familiar size, cast shadows, occlusion, accommodation, texture gradient, linear perspective, aerial perspective, shading, lighting, and defocus blur, etc.

Motion parallax is a monocular depth cue in which an individual views objects that are closer to the individual as moving faster than objects that are further away from the individual. For instance, when an individual moves relative to stationary objects, the apparent relative motion of the objects with respect to each other and/or with respect to a background can provide the individual information about the relative distance between the objects.

The relative size of two objects can be used by an individual as a monocular depth cue. For example, if two objects are known to be the same size but their absolute size is unknown, relative size cues can provide information about the relative depth of the two objects. If one object appears larger than the other, the object which appears larger angle appears to be closer to the individual.

If an individual has previous knowledge of the actual size of an object (familiar size), then this knowledge can be used as a monocular depth cue to determine the absolute depth of the object. For example, prior knowledge of the actual size of an object can be combined with the visually perceived size of the object to determine the absolute depth of the object.

Cast shadows can also be used by an individual as a monocular depth cue. For example, the shadows that are cast by objects may provide a cue to determine the shape of the object and its position in space.

Occlusion (also referred to as interposition) is a monocular depth cue that occurs when near surfaces overlap far surfaces. For example, if one object partially blocks the view of another object, the individual will perceive it as closer.

Accommodation may also be used by an individual as a monocular depth cue. Accommodation is related to the kinesthetic sensation of contractions and relaxations in the ciliary muscles (intraocular muscles) as the eye focuses on objects at different depths. The kinesthetic sensations can be perceived by the visual cortex where they can be used for interpreting distance/depth relative to the individual.

Texture gradient is a monocular depth cue where fine details on objects closer to the individual can be seen more clearly by the individual, whereas such details are not as clearly visible on objects further away from the individual.

Linear perspective is a monocular depth cue where parallel lines converge in the distance, e.g., at infinity, which allows an individual to reconstruct the relative distance of two parts of an object, or of landscape features.

Aerial perspective may also be used as a monocular depth cue. For instance, due to light scattering by the atmosphere, objects that are further away from an individual may have lower luminance contrast and lower color saturation. Thus, objects may seem hazy the farther they are away from the individual. Objects in the foreground (closer to the individual) may have a higher (relative) contrast, and objects in the background (farther away from the individual) may have a lower (relative) contrast. In some cases, objects differing only in their contrast may appear to be at different depths. In addition, the color of distant objects may also be shifted toward the blue end of the spectrum.

Shading and lighting can also be used by an individual as monocular depth cues. For example, the way that light falls on an object and reflects off its surfaces may provide cues to determine the shape of the object and its position in space.

Because the depth of focus of the eye may be limited, defocus blur can be used as a monocular depth cue. For example, objects farther away from on individual may be perceived less clearly (may be blurry) than objects closer to the individual.

In certain instances, a binocular cue is presented to both eyes of the individual and may include any suitable binocular depth cue, such as, without limitation, binocular disparity and vergence. The binocular cue may be two different images of the same object presented in slightly different angles to each eye so as to simulate the object in three-dimensions. For example, in binocular disparity, information derived from the different projection of objects onto each retina can be used to judge depth. By using two images of the same scene obtained from slightly different angles, an individual can triangulate the distance to an object because each eye views a slightly different angle of the object seen by the left and right eyes due to the horizontal separation parallax of the eyes. If an object is farther away from the individual, the disparity of the images seen by both eyes will be small, but if the object is closer to the individual, the disparity will be larger.

Vergence (also referred to as convergence) may also be used by an individual as a binocular depth cue. Vergence is related to the kinesthetic sensation of movements in the extraocular muscles as the eyes focus on the same object. For instance, the kinesthetic sensations due to binocular disparity can be perceived by the visual cortex where they can be used for interpreting distance/depth relative to the individual.

A depth cue may have a certain strength, which represents a measure of how much the depth cue contributes to the perception or sensing of depth by the individual. The strength of a depth cue may be related to the relative intensity of the depth cue (e.g., cast shadows, texture gradient, linear perspective, aerial perspective (e.g., contrast), shading, lighting, defocus blur, binocular disparity, etc.), and/or may be related to the number of different depth cues presented to the individual. For instance, a "stronger" depth cue may be related to a depth cue presented at a relatively higher intensity to the individual, and/or may be related to a larger number of different depth cues that are presented to the individual from a set of possible depth cues. Conversely, a "weaker" depth cue may be related to a depth cue presented at a relatively lower intensity to the individual, and/or may be related to a smaller number of different depth cues (or a single depth cue) presented to the individual from a set of possible depth cues. The strength of the depth cues may be correlated with the difficulty level of a depth-perception task presented to an individual. A depth-perception task where the object is associated with stronger depth cues may be have a lower difficulty level, and thus be relatively easier for the individual to perform (e.g., the individual may more readily complete the depth-perception task or may progress further towards completion of the depth-perception task). A depth-perception task where the object is associated with weaker depth cues may be have a higher difficulty level, and thus be relatively harder for the individual to perform (e.g., the individual may not complete the depth-perception task or may not make as much progress towards completion of the depth-perception task).

In certain embodiments, the orthoptic method includes titrating the strength of a depth cue. The method may include titrating the strength of one or more monocular depth cues presented to the user. In some instances, the method may include titrating the strength of one or more binocular depth cues presented to the user. As described herein, titrating a depth cue may include adjusting (e.g., weakening or strengthening) the depth cue. In some cases, the titrating includes weakening or strengthening the depth cue (e.g., one or more monocular depth cues) based on the performance of the individual for performing the one or more depth-perception tasks. For example, the titrating may be based on how accurately the individual is visually perceiving depth at the current strength of the depth cue. Titrating the strength of the depth cue may thus change the accuracy with which the individual is visually perceiving depth to a desired level or within a desired range. For instance, reducing the strength of a monocular depth cue may result in the individual relying more on binocular depth cues to perform a depth-perception task during the orthoptic method.

As an example, the strength of the depth cues, represented in FIG. 1 by the size of the rectangles, indicates the level of contribution of the monocular and binocular depth cues to the user's perception of the object's depth characteristics. Thus, the difficulty of performing a depth-perception task by the user is correlated with the ability of the user to perceive the depth of the objects based on the strength of the monocular and/or binocular depth cues. The strength of a depth cue is defined by whether it is present or not, and when present, by how reliable it is as an indicator of the depth of the stereoscopic object. For instance, motion parallax depth cues may be weakened by randomizing the speed of a stereoscopic object; size-related depth cues (relative and familiar size) can be weakened by randomizing the physical sizes of the stereoscopic object; and cast shadows may be weakened by increasing the strength of an ambient light source relative to a point light source.

As time progresses during performance of the orthoptic method, the strength, e.g., relative strengths, of the monocular and binocular depth cues may be altered in any suitable manner. If the user does not achieve one or more of the depth-perception tasks 100, the user may be presented the same depth-perception task or may be presented with a different depth-perception task having the same or a similar (or lower) difficulty level. When the user achieves one or more depth-perception tasks 100, the strength of the monocular depth cue 120 may be reduced 122, while the binocular depth cue strength 140 is maintained 142, making the monocular depth cue a less reliable source of information for the user to perceive the three-dimensional properties of the object 112 during a second time interval during which one or more depth-perception tasks 102 are presented. The change in the depth cue strength may also occur randomly (e.g., increasing or decreasing the difficulty level), regardless of whether the user has or has not performed a depth-perception task. As the strength of the monocular depth cue is reduced, the user may be forced to rely more on the binocular depth cues to perform the depth-perception tasks.

If the user does not achieve one or more of the depth-perception tasks 102 presented during the second time interval, the user may be presented the same depth-perception task or may be presented with a different depth-perception task having the same or a similar (or lower) difficulty level. When the user achieves one or more depth-perception tasks 102 during the second time interval, the strength of the monocular depth cue 122 may be reduced or one or more of the monocular depth cues may be removed, while the binocular depth cue strength 142 is maintained 144, making the monocular depth cue a less reliable source of information for the user to perceive the three-dimensional properties of the object 114 during a third time interval during which one or more one or more depth-perception tasks 104 are presented.

For example, the monocular depth cue may be removed during a third time interval during which one or more the depth-perception tasks 104 are presented, and thus the user is forced to rely only on the binocular depth cue 144 to perceive the three-dimensional properties of the object 114.

Whether the user has performed the depth-perception tasks can be determined by receiving an input from the user, e.g., through an input device such as a mouse, keyboard, touchpad, touchscreen, joystick, gamepad, trackball, and the like, or combinations thereof, etc., and determining whether the input is sufficient to complete the task. The input received from the user may indicate whether the user has progressed toward a goal (e.g., completion of the depth-perception task(s)). For instance, the input received from the user may indicate the difficulty level experienced by the user. In some cases, if the input received from the user indicates that the task has not been completed, then this may be an indication of a relatively higher difficulty level experienced by the user. In other instances, if the input received from the user indicates that the task has been completed, then this may be an indication of a relatively lower difficulty level experienced by the user. Based on the inputs received from the user, the difficulty level of the task may be changed (e.g., weakened or strengthened). For example, if the input from the user at a time point during the first time interval indicates a relatively low difficulty level, then the initial monocular depth cue may be weakened to a second monocular depth cue strength after the time point. The time point for changing the strength of the depth cue may be chosen arbitrarily or may be chosen based on the difficulty level experienced by the user prior to the time point. In some cases, the time point for changing the difficulty level is chosen so as to maintain a threshold level of difficulty experienced by the user before and after the time point.

In some cases, when the input is sufficient to indicate completion of the task, a feedback may be provided to the user to inform the user that the task has been performed. Thus, the method may include providing the user a feedback that notifies the user whether there has been progress toward the goal. The feedback may be any suitable form of feedback, including, but not limited to, a change in the image on the user interface, a sound, a vibration, combinations thereof, and the like.

A collection of tasks may be organized into a goal for the individual to achieve. Thus, as the individual performs the tasks within the collection of tasks, the input from the individual can indicate how much the individual has progressed toward the goal. The feedback may in some cases indicate the extent to which the individual has progressed toward the goal. Achievement of a goal may be measured against a threshold level, where completion of a number of tasks that is above a threshold number of tasks indicates achievement of the goal, whereas completion of a number of tasks that is below the threshold number of tasks indicates that the goal has not been achieved. In some cases, if the individual does not achieve the goal, the individual may be presented a collection of depth-perception tasks having the same or a similar (or lower) difficulty level. However, if the individual achieves the goal, then the individual may be presented with a collection of depth-perception tasks having a higher difficulty level.

Figure 2:
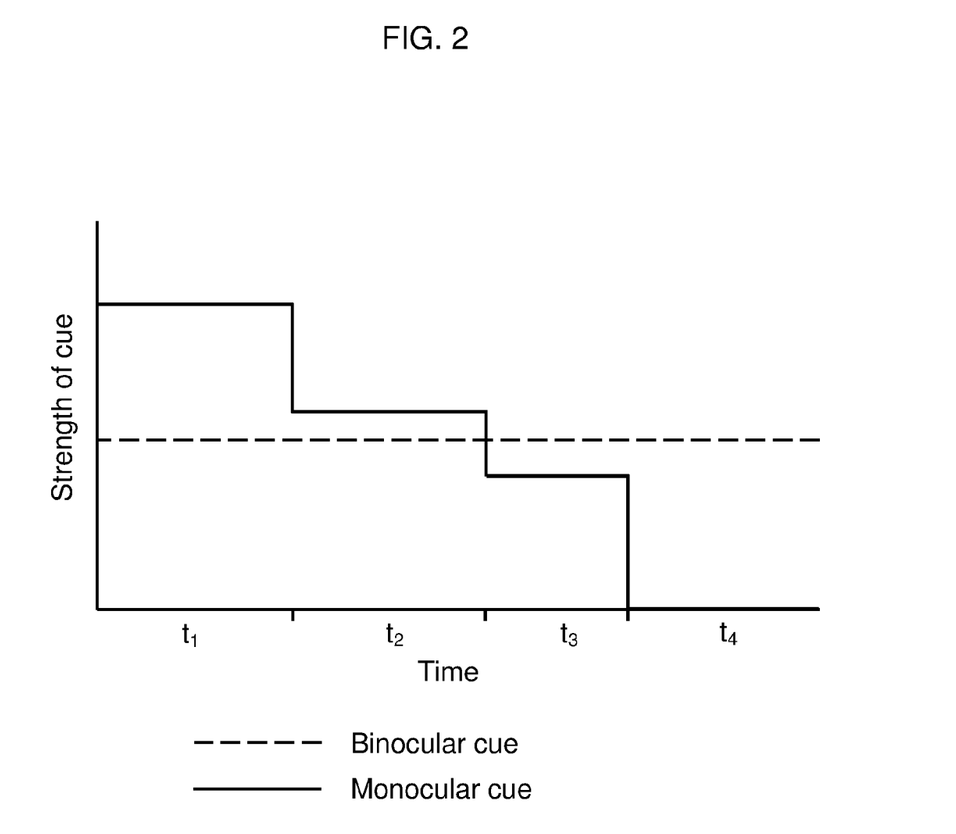
FIG. 2 shows a schematic diagram showing the change in the strength of depth cues during a stereoscopic task, according to embodiments of the present disclosure.

The different time intervals, as described above, may be discrete time intervals defined by a length of time and a step-wise change in depth cue strengths. For example as shown in FIG. 2, the strength of the monocular depth cue may be stronger than the strength of the binocular depth cue during an initial time period $t_1$, and thus the user's perception of the depth of an object associated with the monocular and binocular depth cues may rely more on the monocular depth cues than the binocular depth cues. The strength of one or more of the monocular depth cues may be reduced progressively in a step-wise manner, e.g., between $t_1$ and $t_2$, $t_2$ and $t_3$, $t_3$ and $t_4$, etc., such that the relative strength of the monocular to binocular depth cues is reduced, and is eventually left with only the binocular depth cue. Alternatively, the change in depth cue strength may be continuous throughout or through at least part of the depth-perception task, which may be represented by a sloped or curved line instead of the straight horizontal and vertical lines in FIG. 2.

The difficulty of performing a depth-perception task experienced by the user may vary and may depend on the user's ability to respond to or make use of the various monocular and binocular depth cues when perceiving the three-dimensional properties of the object in the user interface. The difficulty may also be correlated with a level of accuracy required of the user in perceiving the depth of an object and responding to the perceived depth. Thus, the higher the required accuracy level, the more precisely the user must be able to perceive and respond to the object depth to perform the task. Thus, the difficulty level of a task can be controlled as desired by changing the strengths of the monocular and/or binocular depth cues of an object and/or by changing the accuracy required for the task to be completed.

In certain embodiments, the depth-perception task has a threshold level of accuracy for the individual to determine a three-dimensional position of the stereoscopic objects. The threshold level of accuracy may be correlated with the difficulty level. As such, the orthoptic method may include changing the threshold level of accuracy over a first time period such that the reduction in the strength of the one or more monocular depth cues is compensated for by the change in the threshold level of accuracy.

Figure 3:
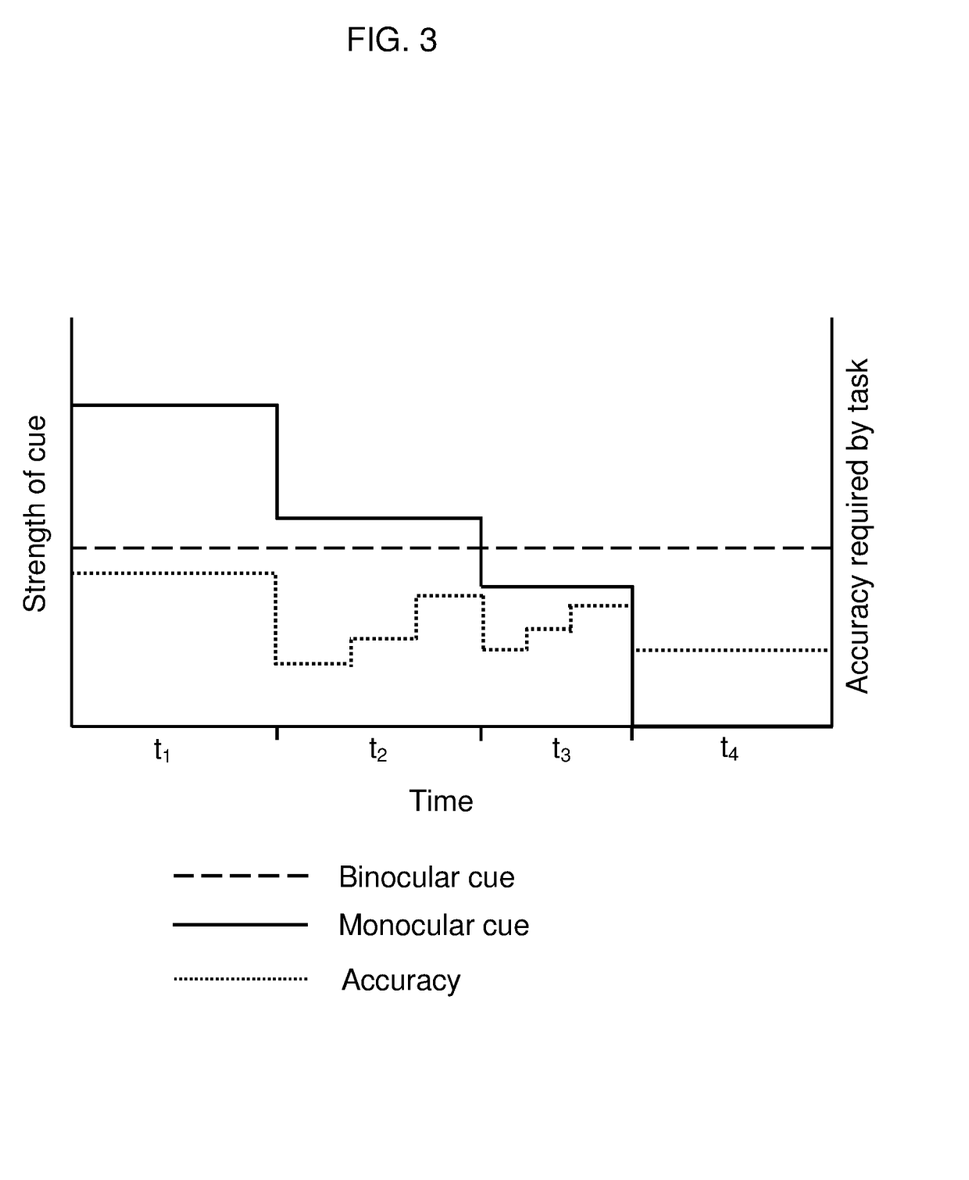
FIG. 3 shows a schematic diagram showing the change in the strength of depth cues and the accuracy required during a stereoscopic task, according to embodiments of the present disclosure.

For example, as shown in FIG. 3, the difficulty level for achieving one or more depth-perception tasks can be controlled such that the accuracy required is changed so as to maintain a difficulty level above a predetermined threshold level. Thus, a reduction in the strength of the monocular depth cue at the end of $t_1$ may be accompanied by a corresponding reduction in the accuracy level required to complete tasks subsequent to the reduction in the strength of the monocular depth cue to compensate for the increase in the difficulty level associated with the reduction in the strength of the monocular depth cue. During $t_1$, the user may adapt and rely more on the binocular depth cue, thereby reducing the experienced difficulty. As that happens, the accuracy required may be increased to increase the difficulty level. At the end of $t_2$, the strength of the monocular depth cue may be further reduced, causing another increase in the difficulty level experienced by the user for performing tasks after $t_2$. This may be compensated for by another reduction in the accuracy level required to perform the tasks, and so on and so forth. As was the case for the strength of the depth cue, the accuracy level required to perform the tasks may be changed in a step-wise manner, or may be changed gradually during any time period, and thus may be represented by a slope or curve instead of the straight lines shown in FIG. 3.

The orthoptic method may also include assessing the stereoacuity (stereoscopic acuity) of the user. The stereoacuity of the user may be assessed based on the user's performance in completing and/or progressing toward completion of one or more depth-perception tasks as described herein. Stereoacuity is the smallest detectable depth difference that can be seen in binocular vision. For instance, stereoacuity is the perceived depth difference between two objects, converted into an angle of binocular disparity, i.e., the difference in their binocular parallax. In some cases, stereoacuity is measured in minutes of arc, and thus the orthoptic method may include assessing the minimum detectable minutes of arc that an individual is able to perceive.

In some embodiments, the orthoptic method includes assessing the motion-in-depth acuity of an individual. Motion-in-depth acuity may depend on changes in binocular disparity over time (CDOT), or may depend on the differences in motion at the left and right eye that occur when objects move in depth. The motion-in-depth acuity of the user may be assessed based on the user's performance in completing and/or progressing toward completion of one or more depth-perception tasks as described herein. In some cases, the motion-in-depth acuity of the user is compared to a threshold value to determine the user's performance.

In certain cases, assessing stereoacuity and/or motion-in-depth acuity of the individual includes presenting one or more n-alternative forced choice tasks to the individual. In these embodiments, the depth-perception task presented to the user may be an n-alternative forced choice task. For example, an n-alternative forced choice task may be used to assess the speed and accuracy of the user in a given timed interval. The user may be presented with two or more alternative choices simultaneously, a delay interval can be measured as the user decides on a response/choice, and the user's response indicating the user's choice can be recorded. For example, the n-alternative forced choice task may be a 2-alternative forced choice task where the user is presented with two alternative choices simultaneously, a delay interval is measured as the user decides on a response/choice, and the user's response indicating the user's choice is recorded.

In some embodiments, assessing stereoacuity and/or motion-in-depth acuity of the individual includes presenting one or more odd-man-out tasks to the individual. An odd-man-out task may be used to assess the speed and accuracy of the user in performing depth perception tasks. Generally, in an odd-man-out task, a user is tasked with selecting an object that has a perceived difference (e.g., a perceived difference in depth) from other objects presented to the user. In some cases, the odd-man-out task is a task for the individual to select, in the user interface, a first stereoscopic object among a plurality of stereoscopic objects based on the perceived difference in depth of the first stereoscopic object relative to the perceived depths of the other stereoscopic objects. In some cases, the odd-man-out task is a task for the individual to select, in the user interface, a second stereoscopic object among a plurality of stereoscopic objects based on a perceived change in depth of the second stereoscopic object relative to the perceived change in depths of the other stereoscopic objects.

In certain embodiments, the n-alternative forced choice task and/or the odd-man-out task defines a difficulty level for the individual to perform the n-alternative forced choice task or the odd-man-out task. The n-alternative forced choice task and/or odd-man-out task difficulty level may be individually titrated, as described herein.

Embodiments of the orthoptic method can also include assessing the depth-perception of the individual at different areas in the individual's visual field. For example, the orthoptic method may include displaying a subset of the one or more stereoscopic objects on the user interface such that the stereoscopic objects in the subset are perceived at a periphery of the individual's visual field. In other instances, the orthoptic method may include displaying a subset of the one or more stereoscopic objects on the user interface such that the stereoscopic objects in the subset are perceived towards the center of the individual's visual field. A mixture of stereoscopic objects can also be displayed on the user interface where one or more stereoscopic objects are perceived at a periphery of the individual's visual field and one or more stereoscopic objects are perceived towards the center of the individual's visual field.

The orthoptic method may further include displaying a second subset of the one or more stereoscopic objects on the user interface such that the stereoscopic objects in the second subset are perceived by the individual to be changing depths. As described herein, changes in depths of the stereoscopic objects in the second subset may be used to assess the depth perception of the individual and/or may be integrated into the depth-perception tasks presented to the individual during the orthoptic method.

In some embodiments, a third subset of the one or more stereoscopic objects includes one or more state-dependent stereoscopic objects that are each in one of two or more states defining a first and second states. A state-dependent stereoscopic object in a first state may be associated with a first state sensory cue that is different from a second state sensory cue associated with the state-dependent stereoscopic object in a second state. In some instances, a state-dependent stereoscopic object alternates among the two or more states at a time interval, such as within the first time period of the orthoptic method. In certain cases, the first state is a permissive state and the second state is a non-permissive state. For example, in some instances, a stereoscopic object in the third subset is displayed on the user interface such that the stereoscopic object is perceived by the individual as being at a different depth from the depths of stereoscopic objects that are not in the third subset.

In certain embodiments, the orthoptic method may be used to reduce an individual's dependence on monocular depth cues for performing depth-perception tasks. Stated another way, the orthoptic method may be used to improve an individual's binocular depth perception for performing depth-perception tasks. As described herein, the orthoptic method includes the step of displaying one or more stereoscopic objects on a user interface as part of one or more depth-perception tasks for an individual to perform. In some instances, the method further includes, before the displaying step, providing the individual, through the user interface, with a training goal for the individual to achieve during a time period (e.g., during a second time period). The training goal may define a difficulty level for achieving the training goal by the individual. In some cases, the orthoptic method also includes displaying on the user interface: a first image to a visual field of a first eye of the individual; and a second image to a visual field of a second eye different from the first eye of the individual. The first and second images may include one or more dichoptically-presented vergence cues. Dichoptically-presented images are images viewed by a separate and independent field by each eye. In dichoptically-presented images, a first image is presented to one eye (e.g., the left eye) and a different image is presented to the other eye (e.g., the right eye). In some cases, the training goal includes fusing the first and second images. The dichoptically-presented vergence cues may define a dichoptically-presented vergence cue strength correlated with the difficulty level. In certain instances, the orthoptic method also includes receiving an input from the individual through the input device, the input indicating whether the individual has achieved the training goal. In some cases, the orthoptic method also includes providing the individual a feedback that indicates to the individual whether the individual has achieved the training goal.

In certain embodiments, the dichoptically-presented cues are corrected to account for the individual's vergence deviation. For example, the individual's vergence deviation can be determined by displaying, on the user interface, a stereoscopic image comprising a stereoscopic object and dichoptic nonius lines. The horizontal displacement of the dichoptic nonius lines can be adjusted such that the dichoptic nonius lines are perceived by the individual to be collinear, thereby obtaining a full correction value for the individual's vergence deviation. In some instances, the orthoptic method includes displaying on the user interface, the stereoscopic image with a correction for the individual's vergence deviation based on the full correction value. The correction can be reduced such that the stereoscopic image is perceived to appear in double, thereby obtaining a lesser correction value for the individual's vergence deviation. In some cases, the individual's vergence deviation is set to be the midpoint between the full and lesser correction values.

As described herein, the orthoptic method includes the step of displaying one or more stereoscopic objects on a user interface as part of one or more depth-perception tasks for an individual to perform. In certain embodiments, the orthoptic method includes, before the displaying step, displaying on the user interface: a first image to a visual field of a first eye of the individual; and a second image to a visual field of a second eye different from the first eye of the individual. In some cases, the first and second images have the same absolute contrast level. The orthoptic method may then include reducing the contrast in the image perceived to have the higher contrast by the individual to reduce the difference in contrast in the images perceived by the first eye and the second eye.

In certain embodiments, the orthoptic method is presented to the user as a game, such as in a video game format. In these embodiments, the user interface may be a video game, where the user interacts with an input device (e.g., mouse, keyboard, touchpad, touchscreen, joystick, gamepad, trackball, and the like, or combinations thereof) to control the actions of one or more objects in the video game. Any suitable type of video game may be used to perform the subject orthoptic methods. Non-limiting examples of such video games include a fixed shooter game, a scrolling shooter game, and the like. Examples of fixed shooter games include, but are not limited to, two-dimensional fixed shooter games (e.g., similar to Space Invaders), two and a half dimensional (also referred to as three-quarter perspective) fixed shooter games, and three-dimensional fixed shooter games. Examples of scrolling shooter games include, but are not limited to, two-dimensional scrolling shooter games (e.g., similar to Tryian), two and a half dimensional (also referred to as three-quarter perspective) scrolling shooter games, and three-dimensional scrolling shooter games. Other types of shooter games may also be used in the subject orthoptic methods, such as, but not limited to, rail shooters, tube shooters, or multi-directional shooters.

Depth-perception tasks presented to the user during the orthoptic method may be part of the video game (e.g., scrolling shooter game). For example, the video game (e.g., scrolling shooter game) may include a user interface comprising a perceived three-dimensional space. The video game may include a depth-perception task where the individual is tasked with aligning a first stereoscopic object and a second stereoscopic object in the perceived three-dimensional space. During the orthoptic method, the user can control (using an input device) a three-dimensional position of the first stereoscopic object in the perceived three-dimensional space. By controlling the position of the first stereoscopic object in the three-dimensional space, the user can align the first stereoscopic object with the second stereoscopic object in the three-dimensional space, and thus progress toward completion of the task and/or goal. As described herein, the difficulty level of the depth-perception task can be weakened or strengthened based on the user's performance. Feedback can also be provided to the user based on the user's performance. An example of feedback includes displaying a score in the video game to the user.

In certain embodiments, the orthoptic method includes positioning a visual display that includes the user interface over a visual field of the individual. The visual display may be configured to display the stereoscopic image comprising the stereoscopic object on the user interface. For instance, the visual display can be any suitable visual display, such as, but not limited to, a television, a computer monitor, an LCD display, an LED display, an OLED display, a headset (e.g., a virtual reality (VR) headset). The visual display can be configured to display two-dimensional images and/or three-dimensional images.

In certain embodiments, the subject method includes a method for treating a condition or disease in an individual. As used herein, the terms "treat," "treatment," "treating," and the like, refer to obtaining a desired pharmacologic and/or physiologic effect. The effect may be prophylactic in terms of completely or partially preventing a disease or condition or symptom thereof and/or may be therapeutic in terms of a partial or complete cure for a disease or condition and/or adverse effect attributable to the disease or condition. "Treatment," as used herein, covers any treatment of a disease or condition in a mammal, particularly in a human, and includes: (a) preventing the disease or condition from occurring in a subject which may be predisposed to the disease or condition but has not yet been diagnosed as having it; (b) inhibiting the disease or condition, i.e., arresting its development; and (c) relieving the disease or condition, e.g., causing regression of the disease or condition, e.g., to completely or partially remove symptoms of the disease or condition.

In some instances, the disease or condition to be treated in the individual is abnormal depth perception. Thus, orthoptic methods of the present disclosure find use in treating individuals who are diagnosed as having abnormal depth perception. In some cases, the individual may be diagnosed with amblyopia. Amblyopia can result from any condition that prevents the eye from focusing clearly. For example, amblyopia can be caused by the misalignment of the two eyes, which is a condition called strabismus. As such, orthoptic methods of the present disclosure find use in treating individuals who are diagnosed as having strabismus. In an individual having strabismus, the eyes can cross in (esotropia) or turn out (exotropia). In some cases, amblyopia may be caused by a clouding of the front part of the eye, which is a condition that may be referred to as a cataract. In other embodiments, the orthoptic method may be used on an individual who has normal depth perception.

Devices

The present method may be implemented on any convenient device containing a visual display containing a user interface configured to display one or more objects associated with a monocular depth cue and a binocular depth cue. For instance, the visual display can be any suitable visual display, such as, but not limited to, a television, a computer monitor, an LCD display, an LED display, an OLED display, a headset (e.g., a virtual reality (VR) headset). The visual display can be configured to display two-dimensional images and/or three-dimensional images. For example, in some cases, the visual display may be part of a headset.

In some embodiments, the orthoptic device is configured to receive an input from the user through an input device. Thus, embodiments of the orthoptic device may include an input device, such as, but not limited to, a mouse, keyboard, touchpad, touchscreen, joystick, gamepad, trackball, and the like, or combinations thereof. The input device may be configured to control one or more aspects of the user interface displayed to the user. For instance, the input device may be configured to control the position of one or more stereoscopic objects displayed on the user interface. As described herein, an individual may use the input device to perform one or more depth-perception tasks presented to the user during an orthoptic method. In some cases, the orthoptic device may have a user interface that can independently control the image displayed to each of the two eyes of the individual.

In certain embodiments, the orthoptic device can contain a processor and a memory location (e.g., a non-transient computer-readable medium) to store software programs (e.g., instructions) that, when executed, instructs the processor to implement the present method on the user interface. In some cases, the instructions for performing the orthoptic method may be saved on a non-transient computer-readable medium. When executed by the processor, the instructions may cause the visual display to display one or more stereoscopic objects on the user interface, and titrate the strength of one or more monocular depth cues, as described herein.

In some embodiments, the components of the orthoptic device (e.g., visual display, processor and non-transient computer-readable medium) are all contained in a single unit. For example, the orthoptic device may be a headset, which contains a visual display, a processor and a non-transient computer-readable medium as described herein. In some instances, the orthoptic device is configured to interface with an input device. The input device and the orthoptic device may be part of a single device, or the input device may be separate from the orthoptic device and connected to the orthoptic device by a wired or wireless connection.

In some embodiments, the orthoptic device is configured to interface with a feedback delivery device, e.g., a vibratory device, speaker, etc., from which a user can receive feedback notifying the user whether there has been progress toward completion of a depth-perception task, as described herein. In some cases, the feedback delivery device is provided in a single unit with the user input device.

A variety of computer-related embodiments are also provided in the subject orthoptic devices. In some embodiments, the orthoptic methods described herein may be performed using a computer, e.g., a processor. Accordingly, provided is a computer-based system for performing the orthoptic methods, for example in order to assess and/or treat an abnormal depth perception in an individual.

In certain embodiments, the orthoptic methods are coded onto a computer-readable medium in the form of "programming", where the term "computer readable medium" as used herein refers to any storage or transmission medium that participates in providing instructions and/or data to a computer for execution and/or processing. Examples of storage media include CD-ROM, DVD-ROM, BD-ROM, a hard disk drive, a ROM or integrated circuit, a magneto-optical disk, a solid-state memory device, a computer readable flash memory, and the like, whether or not such devices are internal or external to the computer. A file containing information may be "stored" on computer readable medium, where "storing" means recording information such that it is accessible and retrievable at a later date by a computer. Examples of media include, but are not limited to, non-transitory media, e.g., physical media in which the programming is associated with, such as recorded onto, a physical structure. Non-transitory media for storing computer programming does not include electronic signals in transit via a wireless protocol.

In certain embodiments, computer programming may include instructions for directing a computer to perform one or more orthoptic method steps as disclosed herein. For example, the computer programming may include instructions for directing a computer to display one or more stereoscopic objects on a user interface, and titrate the strength of one or more monocular depth cues, as described herein. In embodiments, the computer programming includes instructions for directing a computer to analyze the acquired performance data qualitatively and/or quantitatively. Qualitative determination includes determinations in which a simple yes/no result is provided to a user with respect to the depth perception performance of the individual. Quantitative determination includes both semi-quantitative determinations in which a rough scale result, e.g., low, medium, high, is provided to a user regarding the depth perception performance of the individual, and fine scale results in which an exact measurement of the depth perception performance of the individual is provided to a user.

With respect to computer readable media, "permanent memory" refers to memory that is permanent. Permanent memory is not erased by termination of the electrical supply to a computer or processor. Computer hard-drive, CD-ROM, DVD-ROM, BD-ROM, and solid state memory are all examples of permanent memory. Random Access Memory (RAM) is an example of non-permanent memory. A file in permanent memory may be editable and re-writable. Similarly, a file in non-permanent memory may be editable and re-writable.

Systems

Also provided herein is an orthoptic system for implementing the present method. The system may include a processor, and a memory location (e.g., a non-transient computer-readable medium) to store software programs (e.g., instructions) that, when executed, instructs the processor to implement the present method. For example, the instructions, when executed by the processor, may cause the processor to display a user interface configured to display one or more stereoscopic objects, where each object is associated with a monocular depth cue and a binocular depth cue, as described herein. The instructions, when executed by the processor, may also cause the processor to titrate the strength of the monocular depth cues, as described herein.

In some embodiments, the orthoptic system is configured to interface with one or more devices not contained within the system itself. For example, the orthoptic system may be configured to interface with a visual display (e.g., where the visual display is separate from the system and is connected to the system by a wired or wireless connection). In some instances, the orthoptic system is configured to interface with an input device (e.g., where the input device is separate from the system and is connected to the system by a wired or wireless connection). The system in some cases is configured to interface with an input device, e.g., a mouse, keyboard, touchpad, touchscreen, joystick, gamepad, trackball, and the like, or combinations thereof, etc. In some embodiments, the system is configured to interface with a feedback delivery device, e.g., a vibratory device, speaker, etc., from which a user can receive feedback notifying the user whether there has been progress toward completion of a depth-perception task, as described herein. In some cases, the feedback delivery device is provided in a single unit with the user input device.

Any combination of the components of the system may be provided on a separate device, e.g., a computer system containing the processor and the memory location and a headset containing the user interface, or the components may all be in a single device. Any suitable arrangement of the combination of the system components may be used.

Figure 4:
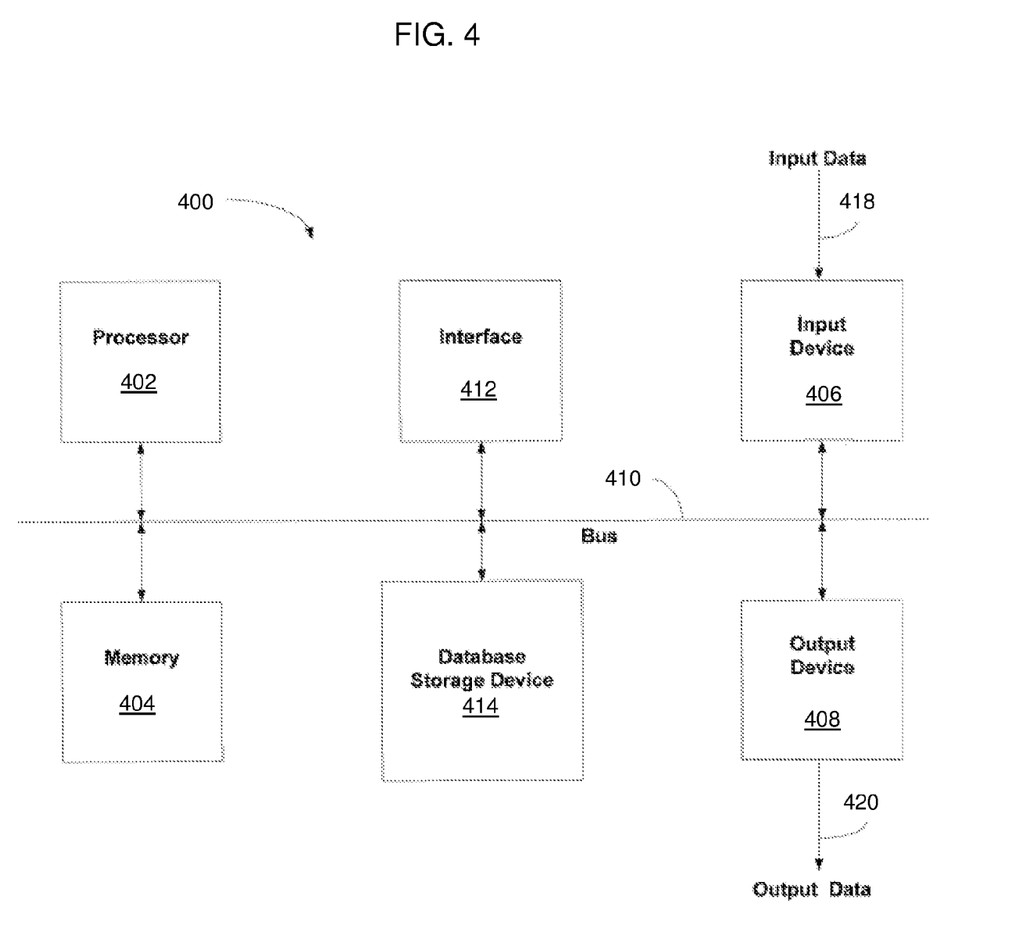
FIG. 4 shows a block diagram showing a computer system for implementing an orthoptic method, according to embodiments of the present disclosure.

A schematic arrangement of an example of an orthoptic system is shown in FIG. 4. The system 400 includes a user interface 412 for displaying the visual objects with a monocular depth cue and a binocular depth cue. The user interface may be any suitable device that includes a visual display, e.g., a headset. The user interface can be controlled by a processor 402, which executes programs, e.g., programs to implement the present method, stored in memory 404. In some cases, the system includes an input device 406, which may be an input device for receiving input from the user, e.g., a mouse, keyboard, touchpad, touchscreen, joystick, gamepad, trackball, and the like, or combinations thereof, etc., or may be an input device for receiving data from a data storage medium, e.g., a compact-disc (CD) read-only-memory (ROM) reader, digital versatile disc (DVD) reader, universal serial bus (USB) reader, Blue-ray Disc™ reader, etc.

In some cases, the system includes an output device, e.g., a feedback delivery device, for providing feedback to the user informing the user as to whether a task has been performed, as described herein. The output device may be a speaker, a vibratory device, etc.

In some cases, the system includes a database storage device 414 to store data related to the user, e.g., medical record, personal information, insurance information, etc., the performance of the user on the depth-perception task, and/or performance of the user on any other task described herein.

The different components of the system may be connected to each other by any suitable means, including through an appropriate bus 410.

The system may also include any other suitable device, e.g., network communication port, wireless communication device, monitor, data acquisition devices, etc.

Kits

Also provided are kits for practicing one or more embodiments of the above-described methods. The subject kits may vary, and may include various components and/or devices. Devices include those mentioned herein with respect to orthoptic devices or components thereof (such as input devices, feedback devices, etc., as described herein). The kit may include one orthoptic device, or in other cases may include two or more orthoptic devices. Each orthoptic device may be provided in separate containers, such that the devices may be used individually as desired. Alternatively, two or more devices may be provided in the same container such that the two or more devices may be used concurrently. In some cases, the kit includes a packaging that contains a device (e.g., one or more devices as discussed above). The packaging may be a sterile packaging configured to maintain the contents of the packaging in a sterile condition.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form would be a computer readable medium, e.g., CD, DVD, Blu-ray, computer readable memory device (e.g., a flash memory), etc., on which the information has been recorded. Yet another form is a website address which may be used via the Internet to access the information at a removed site. Any convenient form of instructions may be present in the kits.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

EXAMPLES

An implementation of the present method, device and system is further described below.

The present disclosure includes a video game that may be played at any suitable location, including a home. For example, the video game may be a scrolling shooter game, e.g., a Tyrian®-like game, but other forms of games are possible. The game places demands on stereo vision and thereby increases stereo capability in stereo-deficient individuals over time. The game also can include force-feedback.

One approach to alleviate stereo deficiency has been to equalize the input from the two eyes to the brain and reduce suppression. However, no significant correlation was found between decreased suppression and improved visual function. Thus, while dichoptic training improves visual acuity and stereopsis in adult amblyopia, reduced suppression is unlikely to be at the root of visual recovery. Training stereopsis directly may provide a more efficient and effective route to recovery.

The video game can contain several game-design elements:

(1) The game can be performed at home, and is fun to play in order to maximize compliance. It can also enable an easy transition to future clinical trials. The game and device on which it is played can be user friendly; may be configured to minimize variations in the subjects' view point relative to the display; and can allow calibration of the 3D rendering parameters to match individual subjects' viewing geometry and optical correction (e.g., glasses with a prismatic correction). The game and device may also minimize suppression on one eye's image in patients with a tendency toward such suppression.

(2) The subject game, devices and methods may require depth judgments of varying degrees of accuracy to perform the tasks embedded in the game.

(3) The subject game, devices and methods may enable titrating the usefulness of monocular depth cues (such as motion parallax and linear perspective). The game can present monocular and binocular depth cues at the beginning of training because the target subjects may have deficient binocular vision and may need the other (monocular) cues to provide a scaffold for learning to better use binocular cues. As the subject's use of binocular cues increases, the game may reduce the usefulness of monocular cues systematically.

(4) Embedded in the game may be stimuli and tasks that allow quantitative assessment of the subject's binocular vision, such as the acuity of their stereo vision.

(5) The subject game, devices and methods may have a modular design so key features can be toggled in or out, allowing game play to be tuned to the subject's needs.

(6) The subject game, devices and methods can include force-feedback.

(7) The subject game, devices and methods may be implemented in a lightweight headset worn by the subject.

A general description of an implementation of the present method is now provided. Similar to Space Invaders, the player controls a spaceship on the bottom of the screen and "enemy" spaceships appear moving from top to bottom in a 3D environment, meaning the spaceships can appear at different depths. The player adjusts the position of his/her spaceship continuously in two dimensions (horizontal and in depth) and/or in three dimensions (horizontal, vertical, and in depth) to shoot a laser burst at the enemy spaceships in straight vertical lines. The player's spaceship must be aligned both horizontally and in depth with an enemy space ship to hit and destroy it. The enemy spaceships occasionally shoot at the player's spaceship and players must avoid being shot or colliding with enemy spaceships by moving their spaceship away from approaching enemies either horizontally or in depth (or vertically). If the laser burst hits an approaching ship, the ship explodes and points are awarded. The laser burst is visible, so all players, even those with poor stereo vision, know whether they hit the target or not. And the feedback indicates whether the player shot too far or too near in depth thus providing ordinal depth information.

The depth of the spaceships can be specified by several monocular depth cues as well as binocular (i.e., stereoscopic) cues. The monocular cues can be weakened or removed to increase the demands on the binocular system. The monocular cues include (1) motion parallax, which can be weakened by randomizing the speeds of the spaceships, (2) relative and familiar size, which can be weakened by randomizing the physical sizes of the spaceships by different amounts, (3) cast shadows, which can be weakened by changing the lighting from point to ambient sources. Other/additional monocular cues may also be used. Monocular cue strength is decreased over time at a rate that maintains subject performance at a reasonably high hit rate. There can be a random element to the decrease in cue strength as well.

Motivation to play is enhanced by adding variability to the game and by increasing difficulty as performance improves. The player's spaceship is attacked by different types of enemies and is able to use different weapons to fight back. Play difficulty is changed by modifying scrolling speed, frequency of enemy firing, number and size of enemy spaceships, and the precision needed for score a "hit". Enemy ships are mixed with civilian ships and penalties applied when civilian ships are destroyed.

Dial-in features: The game will allow control over a number of key parameters including the balance of foveal/peripheral, crossed/uncrossed disparity, and constant-depth/motion-in-depth challenges. Peripheral challenges will be programmable by including on some "trials" a special spaceship that players are highly motivated to foveate while shooting at other enemies. This spaceship can be destroyed by a simple key-press, but only when its armor is periodically and briefly deactivated as indicated by a high-resolution cue on the spaceship, so that fixation is needed. Placing the spaceship progressively away (in eccentricity) from the other enemies will favor peripheral stereopsis. Similarly, by placing the special spaceship (with armor deactivation) more often far in depth or more often close in depth (relative to the other enemies), the game will train both crossed and uncrossed stereo systems. Finally, enemy spaceships will move either at constant depth or with approaching or receding depth, the latter being hittable only if players can extrapolate the spaceships' motion-in-depth. The balance between peripheral/foveal, crossed/uncrossed and constant or changing depth challenges will be part of the control interface so as to be adaptable to the player's stereo profile.

Toggled features: The game can include features that can be toggled on or off for different groups of subjects.

Contrast equalization: For patients with significant binocular suppression (many amblyopes), the game can include a contrast-equalization phase at the beginning of each session. In this phase, a dichoptic figure will be presented and subjects will decrease the contrast of the image in their dominant eye to make that image appear to have the same contrast as the image in their non-dominant eye.

Vergence training—Continuous modulation of vergence challenge: For individuals with deviated vergence (strabismus or large heterophoria), the game can include an optional feature to (a) correct for a player's deviation while (b) progressively and automatically reducing the correction to train vergence. When turned on, the option will correct for subject's deviation by shifting the left- and right-eye images in software. The correction can be determined as follows. At the beginning of each session, a binocular figure will be displayed on the screen. The player will use the mouse to adjust the relative horizontal displacement of nonius lines displayed next to the figure until they appear collinear. This will provide a measure of the player's resting fixational vergence deviation. The figure will then be displayed with full correction for this deviation and subjects will use the mouse to reduce the correction until the figure appears double, defining the minimum correction the player can tolerate. The software correction used for the session will be set to the midpoint between the "resting" correction and the minimum tolerated corrections. A gradually decreasing correction in the game is anticipated.

Modes and Levels Progression: The principal mode of game play will be in 3D with stereoscopic viewing—a Stereo mode; however, the stereoscopic training can be preceded with a training phase designed to decrease the binocular suppression that is common in amblyopia and to improve fusion and vergence using a 2D fusional training mode of game play designed to accomplish this purpose.

Fusional Training Mode: This mode is a non-stereoscopic, dichoptic version of the game in which the player's spaceship will be presented to one eye and the enemies will be displayed to the other eye. The subject's success will be based on matching the position of their spaceship to that of the enemy in the horizontal direction, but not in depth. Because hitting a target requires aligning the dichoptically presented spaceships, accurate performance requires proper vergence. To aid fusion, a binocular frame will be drawn around the scene as a fusion lock. Strong cues will be presented dichoptically to help vergence—Vertical dashed lines will be displayed dichoptically throughout the background so that they assemble into continuous lines when the player's vergence (with the optional software correction for subjects' vergence deviation) is equal to the game plane. Players will learn that aligning the dashed lines is helpful to achieve good game performance. Early levels in this phase can be easy (few enemy spaceships moving slowly, low precision of aiming needed, etc.). Difficulty can increase as performance improves.

Stereo mode: In this mode, subjects will view the game stereoscopically with each eye receiving a full image. Initially, all monocular cues can be presented and will be reliable. The next levels can gradually increase the demand on the player's stereovision by decreasing the usefulness of the monocular depth cues. Game difficulty is determined on the one hand by its dynamic and accuracy demands, and on the other hand by the subject's ability to judge target depth. To vary difficulty, the accuracy demands can initially be modulated to compensate for the changes in difficulty associated with each reduction in the usefulness of monocular cues. Thus, from the player's point of view, difficulty will continue to increase as they improve. In the final stages of the game, the only reliable available cues to target depth will be binocular cues.

Continuous Assessment: The game can have embedded quantitative assessments of stereoacuity and acuity for motion-in-depth. The first assessment can use a variant of an odd-man-out task embedded in the game as a bombing task. Multiple spaceships will scroll vertically down the screen at a fixed depth relative to the background. The player must bomb an enemy spaceship—defined as the spaceship that is at a different depth than the others—by placing their spaceship over the enemy. Monocular cues can be made non-informative. If players do not drop the bomb on one of the spaceships before they disappear, their spaceship will explode with a large point penalty, forcing them to choose before the trial is over. The second assessment is similarly analogous to an odd-man-out task. A line of spaceships will fly over the background at different depths. Friendly spaceships will move at a fixed depth, while the enemy spaceship will move away from or toward the background. The player's goal is to bomb the enemy as soon as they detect its odd-man-out motion. If they do not do it in time, the enemy will drop a bomb and the player will lose points. Data from assessment blocks can be used to estimate subject's stereoacuity and motion-in-depth acuity. In some cases, no indication is given to players that these are assessment blocks. Short assessment blocks can be distributed throughout a playing session with settings for the enemy spaceship set using the same type of adaptive procedure used for a standard n-alternative forced-choice task.

Compliance: Game access can be password protected which will decrease the probability that people other than the subject access the game. The start and end time of each session can be recorded. Performance in the game and in the in-game assessments can be recorded. A built-in camera can allow a user to confirm that the player is the intended subject.

All publications and patent applications cited in this specification are herein incorporated by reference as if each individual publication or patent application were specifically and individually indicated to be incorporated by reference.

While embodiments of the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. An orthoptic method comprising:
   i) displaying one or more stereoscopic objects on a user interface configured to present one or more depth-perception tasks for an individual to perform during a first time period, wherein each of the one or more depth-perception tasks has a difficulty level for the individual to perform each of the one or more depth-perception tasks, and each stereoscopic object is associated with one or more monocular depth cues and one or more binocular depth cues, and wherein a strength of the monocular depth cues is correlated with the difficulty level; and
   ii) titrating the strength of the monocular depth cues during the first time period in a manner sufficient to reduce a dependence of the individual on the monocular depth cues for performing the one or more depth-perception tasks.

2. The method of claim 1, wherein the monocular depth cues comprise one or more of motion parallax, relative size, familiar size, cast shadows, occlusion, accommodation, texture gradient, linear perspective, aerial perspective, shading, lighting, and defocus blur.

3. The method of claim 1, wherein the binocular depth cues comprise binocular disparity and/or vergence.

4. The method of claim 1, wherein the titrating step ii) comprises weakening or strengthening the monocular depth cues based on a performance of the individual for the one or more depth-perception tasks.

5. The method of claim 1, wherein the titrating step ii) comprises weakening or strengthening the monocular depth cues in a step-wise manner.

6. The method of claim 1, wherein the method further comprises receiving an input from the individual through an input device, wherein the input indicates whether the individual has progressed toward a goal.

7. The method of claim 6, wherein the method further comprises providing the individual a feedback that notifies the individual whether there has been progress toward the goal.

8. The method of claim 6, wherein the goal comprises a plurality of depth-perception tasks to be performed by the individual.

9. The method of claim 6, wherein the input indicates the difficulty level experienced by the individual, and the titrating step ii) comprises weakening an initial monocular depth cue prior to a time point during the first time period to a second monocular depth cue strength after the time point, wherein the time point is chosen arbitrarily or is chosen based on the difficulty level experienced prior to the time point.

10. The method of claim 9, wherein the time point is chosen so as to maintain a threshold level of difficulty before and after the time point.

11. The method of claim 1, wherein the depth-perception task is part of a scrolling shooter game.

12. The method of claim 11, wherein the scrolling shooter game comprises a task for the individual to align a first stereoscopic object and a second stereoscopic object in a perceived three-dimensional space in the user interface by having the individual control a three-dimensional position of the first stereoscopic object in the perceived three-dimensional space.

13. The method of claim 1, wherein the method further comprises assessing stereoacuity and/or motion-in-depth acuity of the individual.

14. The method of claim 13, wherein the assessing stereoacuity and/or motion-in-depth acuity comprises presenting one or more n-alternative forced choice tasks, or one or more odd-man-out tasks to the individual through the user interface.

15. The method of claim 14, wherein the odd-man-out task comprises a task for the individual to select, in the user interface:
   first stereoscopic object among a plurality of stereoscopic objects based on the perceived difference in depth of the first stereoscopic object relative to the perceived depths of the other stereoscopic objects; and/or
   a second stereoscopic object among a plurality of stereoscopic objects based on a perceived change in depth of the second stereoscopic object relative to the perceived change in depths of the other stereoscopic objects.

16. The method of claim 14, wherein the n-alternative forced choice task or odd-man-out task defines a difficulty level for the individual to perform the n-alternative forced choice task or odd-man-out task, and the n-alternative forced choice task or odd-man-out task difficulty level is individually titrated.

17. The method of claim 1, wherein the displaying comprises displaying a first subset of the one or more stereoscopic objects on the user interface such that the stereoscopic objects in the first subset are perceived at a periphery of the individual's visual field.

18. The method of claim 1, wherein the displaying comprises displaying a second subset of the one or more stereoscopic objects on the user interface such that the stereoscopic objects in the second subset is perceived by the individual to be changing depths.

19. The method of claim 1, wherein a third subset of the one or more stereoscopic objects comprises one or more state-dependent stereoscopic objects that are each in one of two or more states defining a first and second states, wherein a state-dependent stereoscopic object in a first state is associated with a first state sensory cue that is different from a second state sensory cue associated with the state-dependent stereoscopic object in a second state, wherein a state-dependent stereoscopic object alternates among the two or more states at a time interval within the first time period.

20. The method of claim 19, wherein the displaying comprises displaying a stereoscopic object in the third subset on the user interface for the stereoscopic object to be perceived by the individual as being at a different depth from depths of stereoscopic objects that are not in the third subset.

21. The method of claim 1, wherein the depth-perception task has a threshold level of accuracy for the individual to determine a three-dimensional position of the stereoscopic objects, wherein the threshold level of accuracy is correlated with the difficulty level, and the method further comprises:
changing the threshold level of accuracy over the first time period such that the reduction in the strength of the one or more monocular depth cues is compensated for by the change in the threshold level of accuracy.

22. The method of claim 1, wherein the method further comprises, before the displaying step i):
1) providing the individual, through the user interface, with a training goal for the individual to achieve during a second time period, wherein the training goal defines a difficulty level for achieving the training goal by the individual;
2) displaying on the user interface:
a first image to a visual field of a first eye of the individual; and
a second image to a visual field of a second eye different from the first eye of the individual,
wherein the first and second images comprise one or more dichoptically-presented vergence cues and the training goal comprises fusing the first and second images, wherein the dichoptically-presented vergence cues define a dichoptically-presented vergence cue strength correlated with the difficulty level;
3) receiving an input from the individual through the input device, the input indicating whether the individual has achieved the training goal; and
4) providing the individual a feedback that indicates to the individual whether the individual has achieved the training goal.

23. The method of claim 22, wherein the dichoptically presented cues are corrected to account for the individual's vergence deviation.

24. The method of claim 23, wherein the individual's vergence deviation is determined by:
displaying, on the user interface, a stereoscopic image comprising a stereoscopic object and dichoptic nonius lines;
adjusting the horizontal displacement of the dichoptic nonius lines such that the dichoptic nonius lines are perceived by the individual to be collinear, thereby obtaining a full correction value for the individual's vergence deviation;
displaying on the user interface, the stereoscopic image with a correction for the individual's vergence deviation based on the full correction value;
reducing the correction such that the stereoscopic image is perceived to appear in double, thereby obtaining a lesser correction value for the individual's vergence deviation; and
setting the individual's vergence deviation to be the midpoint between the full and lesser correction values.

25. The method of claim 1, wherein the method further comprises before the displaying step i):
displaying on the user interface:
a first image to a visual field of a first eye of the individual; and
a second image to a visual field of a second eye different from the first eye of the individual,
wherein the first and second images have the same absolute contrast level; and
reducing the contrast in the image perceived to have the higher contrast by the individual to reduce the difference in contrast in the images perceived by the first eye and the second eye.

26. The method of claim 1, wherein the feedback is a visual, tactile and/or auditory feedback.

27. The method of claim 1, wherein the method comprises positioning a visual display comprising the user interface over a visual field of the individual, wherein the visual display is configured to display the stereoscopic image comprising the stereoscopic object on the user interface.

28. The method of claim 1, wherein the individual is diagnosed as having abnormal depth perception.

29. The method of claim 28, wherein the individual is diagnosed with amblyopia and/or strabismus.

30. The method of claim 1, wherein the individual has a normal depth perception.

31. An orthoptic device for preforming the method of claim 1, the device comprising:
a visual display comprising a user interface configured to display one or more stereoscopic objects to the individual, each stereoscopic object associated with one or more monocular depth cues and one or more binocular depth cues;
a processor; and
a non-transient computer-readable medium comprising instructions that, when executed by the processor causes the visual display to:
display the one or more stereoscopic objects on the user interface; and
titrate the strength of the one or more monocular depth cues.

32. The device of claim 31, wherein the device is configured to receive an input from the individual through an input device.

33. The method of claim 1, wherein the first time period is a time allocated to the individual to perform one or more depth-perception tasks.

34. An orthoptic system comprising:
a processor;
a user interface configured to display one or more stereoscopic objects to an individual and further configured to present one or more depth-perception tasks for an individual to perform during a first time period, wherein each of the one or more depth-perception tasks has a difficulty level for the individual to perform each of the one or more depth-perception tasks, and each stereoscopic object is associated with one or more monocular depth cues and one or more binocular depth cues, and wherein a strength of the monocular depth cues is correlated with the difficulty level; and
a non-transient computer-readable medium comprising instructions that, when executed by the processor causes the user interface to:
  display the one or more objects on the user interface; and
  titrate the strength of the monocular depth cues during the first time period in a manner sufficient to reduce a dependence of the individual on the monocular depth cues for performing the one or more depth-perception tasks.

35. The system of claim 34, wherein the system is configured to interface with an input device configured to receive an input from the individual.

36. The system of claim 34, wherein the system is configured to interface with a feedback delivery device configured to provide a feedback to the individual based on the received input.

37. The method of claim 34, wherein the first time period is a time allocated to the individual to perform one or more depth-perception tasks.

\* \* \* \* \*

UNITED STATES PATENT AND TRADEMARK OFFICE
CERTIFICATE OF CORRECTION

PATENT NO. : 10,500,124 B2
APPLICATION NO. : 15/748578
DATED : December 10, 2019
INVENTOR(S) : Levi et al.

Page 1 of 1

It is certified that error appears in the above-identified patent and that said Letters Patent is hereby corrected as shown below:

In the Specification

At Column 1, Lines 14-16:
"This invention was made with government support under Grant Number RO1EY020976 awarded by the National Eye Institute. The government has certain rights in the invention."

Should read:
-- This invention was made with government support under EY020976 awarded by the National Institutes of Health. The government has certain rights in the invention. --

Signed and Sealed this
Tenth Day of March, 2020

Andrei Iancu
*Director of the United States Patent and Trademark Office*